United States Patent
Prochazka et al.

[19]

[11] Patent Number: 5,911,693
[45] Date of Patent: Jun. 15, 1999

[54] DIFFERENTIAL MYOMETER

[75] Inventors: Arthur Prochazka, Edmonton; David Bennett, Kanata, both of Canada

[73] Assignee: University of Alberta, Edmonton, Canada

[21] Appl. No.: 08/875,385

[22] PCT Filed: Jan. 4, 1996

[86] PCT No.: PCT/CA96/00006

§ 371 Date: Sep. 29, 1997

§ 102(e) Date: Sep. 29, 1997

[87] PCT Pub. No.: WO96/20644

PCT Pub. Date: Jul. 11, 1996

[30] Foreign Application Priority Data

Jan. 4, 1995 [GB] United Kingdom ................. 9500064

[51] Int. Cl.[6] .............................................. A61B 5/103
[52] U.S. Cl. .................................. 600/587; 600/595
[58] Field of Search .............................. 600/587, 595; 73/379.01

[56] References Cited

U.S. PATENT DOCUMENTS

| | | | |
|---|---|---|---|
| 3,972,038 | 7/1976 | Fletcher et al. ................ | 340/189 M |
| 4,337,780 | 7/1982 | Metrick ............................ | 600/487 |
| 4,492,234 | 1/1985 | Arkans ............................. | 600/490 |
| 4,586,387 | 5/1986 | Morgan et al. .................. | 73/862.05 |
| 5,012,817 | 5/1991 | Zeilinski et al. ................ | 600/587 |
| 5,429,140 | 7/1995 | Burdea et al. ................... | 600/587 |
| 5,551,438 | 9/1996 | Moses .............................. | 600/485 |
| 5,581,484 | 12/1996 | Prince ............................. | 364/559 |

FOREIGN PATENT DOCUMENTS 0211984  3/1987  European Pat. Off. .
WO9014042  11/1990  WIPO .

OTHER PUBLICATIONS

J. Ghika et al, Portable System for Quantifying Motor abnormalities in Parkinson's Disease, IEEE Transactions on Biomedical Engineering, vol. 40, No. 3, Mar. 1993.

*Primary Examiner*—Max Hindenburg
*Assistant Examiner*—Charles Marmor, II
*Attorney, Agent, or Firm*—Sawyer & Associates

[57] ABSTRACT

A myometer is disclosed. The myometer, especially in the form of a force-sensing mitt or cuff, may be used to grasp a limb or other object, and particularly used by a clinician in evaluating the medical state of a limb. The myometer has pressure measuring means at at least two locations to provide quantitative information on pressure applied to the limb or object. Preferably, the pressure is measured by at least two pressure transducers, with especially the difference in pressure being measured. The myometer is particularly in a form capable of fitting on a person's hand, with pressure sensitive pads being located at positions corresponding to thumb and to fingers of the hand.

13 Claims, 3 Drawing Sheets

DIFFERENTIAL MYOMETER

FIELD OF THE INVENTION

The present invention relates to a device for measuring the force applied to an object, especially a person's limb, and more particularly to a force-sensing mitt or cuff to be worn or grasped by an evaluator e.g. a clinician, when applying force to a limb. In particular, the invention relates to a mitt or cuff to be worn by an evaluator, with which the evaluator grasps the limb and imposes force on the limb, with the mitt or glove measuring the resultant or net force applied to the limb. The device is particularly intended for use by neurologists, sports clinicians, physiotherapists, occupational therapists and sports trainers to quantify limb force and stiffness as part of an evaluation of motor function. The device could be used elsewhere, where an object is gripped and the force applied is to be monitored.

BACKGROUND OF THE INVENTION

Several known systems use force transducers of different types to monitor force applied manually to a limb. In most cases, force is measured uni-directionally i.e. the push-force or the pull-force is measured, but not both, through a pad or plate applied to a limb. This type of clinical device does not allow the force to be measured during both the push and pull phases of testing cycles characteristic of a clinical evaluation. Some myometers allow for push or pull measurement but this requires the use of either a pad for push or a hook for pull. Numerous laboratory-based systems have been described in which limbs are held in a cast or cradle, and a force transducer measures push-pull forces applied to the cast. Methods of measuring the dynamic characteristics of muscle rigidity, strength and tremor in the upper extremity are described by J. Ghika et al in IEEE Trans. Biomed. Eng. 40, pages 276–283 (1993) and by M. P. Caligiuri in Movement Disorder, Vol. 9, pages 57–63 (1994). Several myometers incorporate bulbs or pads inflated with air or fluid. Force applied to the bulb or pad is measured indirectly by a pressure transducer sensing pressure in a port or tube leading from the bulb.

U.S. Pat. No. 4,337,780 discloses an evaluator's glove having pads attached to the fingertip and palm areas. The evaluator operates a valve to selectively connect one or the other of the pads to a pressure transducer. The force applied to the selected pad is evaluated. IEEE Transactions on Biomedical Engineering 35 (1988) December p. 1091–1093, discloses a plurality of force-sensing elements attached to the fingertips of a clinician performing vaginal delivery of babies. The contribution of the individual fingers to the total grasping force is monitored.

None of these devices allow a clinician to grasp the limb between thumb and fingers and apply cyclical push and pull forces. This is a crucial difference, because in order to evaluate limb stiffness, it is important for the evaluator to cycle the limb back and forth through the full range of motion, while supporting it in a manual grasp. To our knowledge, no myometer exists which ignores the internal force of the grasp while registering the resultant force exerted on the limb.

SUMMARY OF THE INVENTION

A device has now been found which permits a clinician to evaluate limb stiffness.

According to an aspect of the present invention, a device in the form of a mitt or cuff is provided which electronically senses the net force applied to a limb or other object grasped by a person wearing the mitt or cuff.

Another aspect of the present invention provides a force-sensing mitt or cuff which may be used to grasp a limb or other object, said mitt or cuff comprising pressure measuring means at at least two locations on said mitt or cuff to provide quantitative information on pressure applied to said limb or object.

In preferred embodiments of the mitt or cuff of the invention, the pressure is measured by at least two pressure transducers, especially in which the difference in pressure is measured.

A further aspect if the invention provides a device in the form of a garment having a first pressure transducer and a second pressure transducer, said first transducer and said second transducer being located on opposed portions of the garment and being capable of contacting opposed sides of an object, each of said pressure transducers being connected to recording means capable of recording pressure measured by the pressure transducers.

BRIEF DESCRIPTION OF THE DRAWINGS

The invention will be illustrated with reference to the embodiments shown in the drawings, in which.

Detailed Description of the Invention

The present invention will be particularly described herein with reference to the aspect which is a force-sensing mitt or cuff.

Figure 1:
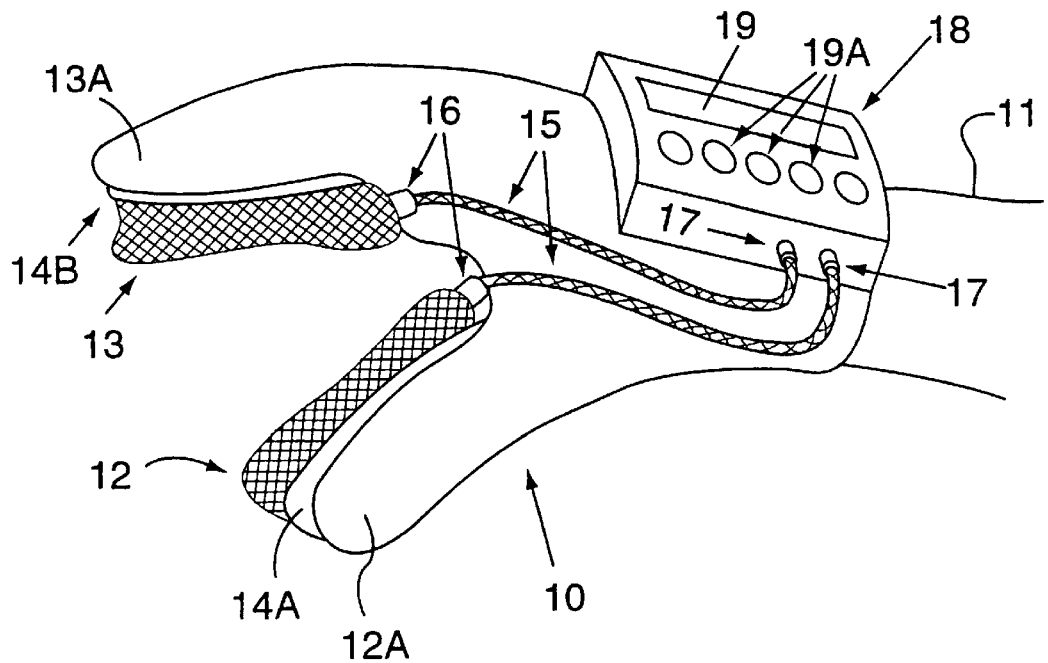
FIG. 1 is a schematic representation of a perspective view of the device according to a preferred embodiment, with an instrumented mitt shown on an evaluator's hand in an open position.

With reference to the Figures, a device for grasping the object to be tested, and for measuring the resultant force applied to the object, is illustrated in FIG. 1. It is to be understood that the object will normally be a limb of a person, with the reason for the testing being to evaluate, determine or monitor the strength or flexibility of a joint in the limb or the strength of muscles in the limb. Such person could be a person who has a physical or other disability, a sporting or other injury, or the device could be used in monitoring progress in a rehabilitation program, a muscle building program or the like. Other related uses will also be found for the device. The device could also find uses away from use with limbs, but use with limbs represents the preferred aspects of the invention.

Figure 4:
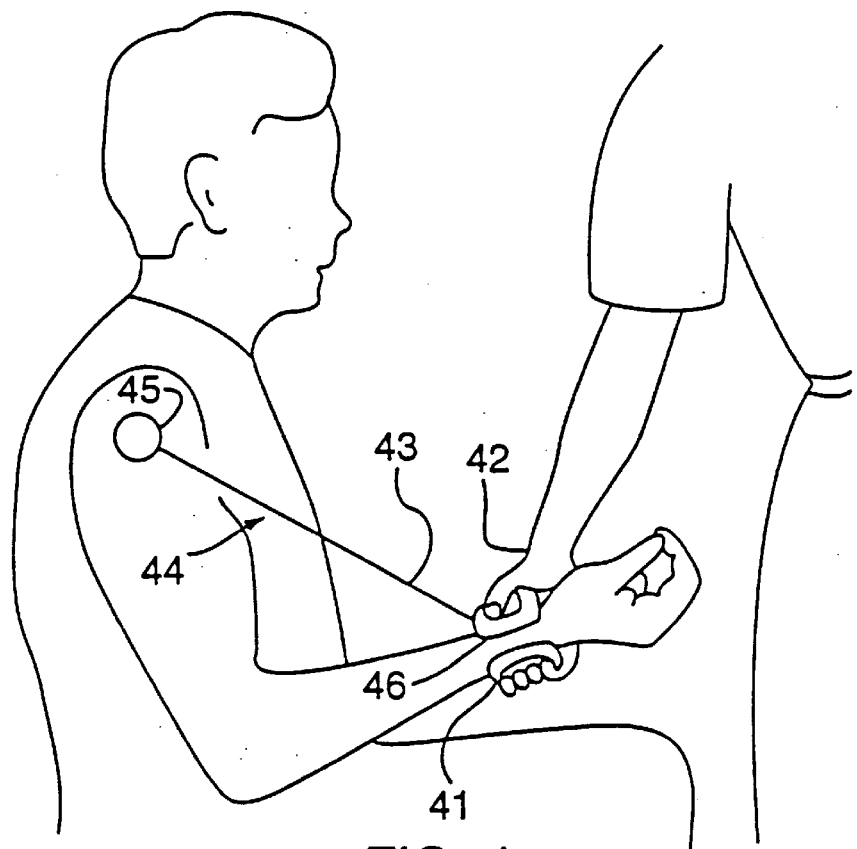
FIG. 4 is a schematic representation of the mitt of FIG. 1 additionally instrumented with a sensor to allow displacement as well as force to be sensed.

As can be seen from FIG. 1, one embodiment of the device takes the form of a mitt worn by an evaluator. An alternative embodiment is the spring-loaded cuff slipped on the subject, as shown in FIG. 4.

In FIG. 1, a mitt 10 is shown on an evaluator's hand 11, which is shown in a open position. In the preferred embodiment, mitt 10 is made of an elastic material such as neoprene.

Fluid or air-filled pressure pads 12 and 13 are located on the inner (palmar) surface of mitt 10, adjacent to the ends of the thumb 12A and finger 13A positions of mitt 10, respectively. Thin, stiff metal sheets 14A and 14B are located between pads 12 and 13 and the elastic material of mitt 10 covering the thumb and fingers, 12A and 13A respectively. Metal sheets 14A and 14B help distribute the force evenly over the surface of each pad.

Tubes 15 connect ports 16 in each of pads 12 and 13 with ports 17 of a differential pressure transducer. The transducer is not shown but is located inside electronic box 18. Electronic box 18 is located on mitt 10 at the location of the back of the evaluator's hand when being worn. In embodiments, the transducer is preferably a Motorola MPX 10 DP or MPX 2010 DP transducer.

Electronic circuitry in box 18 converts the resistance changes of the pressure transducer into a time-varying voltage signal. In the preferred embodiment, the circuitry is in the form of a simple Wheatstone bridge circuit with appropriate amplification and offset controls. Parameters of the force signal e.g. peak to peak variation, maximal and minimal levels, are computed by a microprocessor, an example of which is a Motorola 68HC11. The microprocessor is located in box 18. The signal is displayed digitally on a small display panel 19 on the top or outer surface of box 18, on the back of the mitt or cuff. Buttons 19A allow different parameters to be selected for display, according to software stored in the microprocessor.

Electrical power for the transducer and its associated circuitry may be obtained from a battery contained within mitt 10 or from a separate power source via leads connected to electronic box 18.

Figure 2:
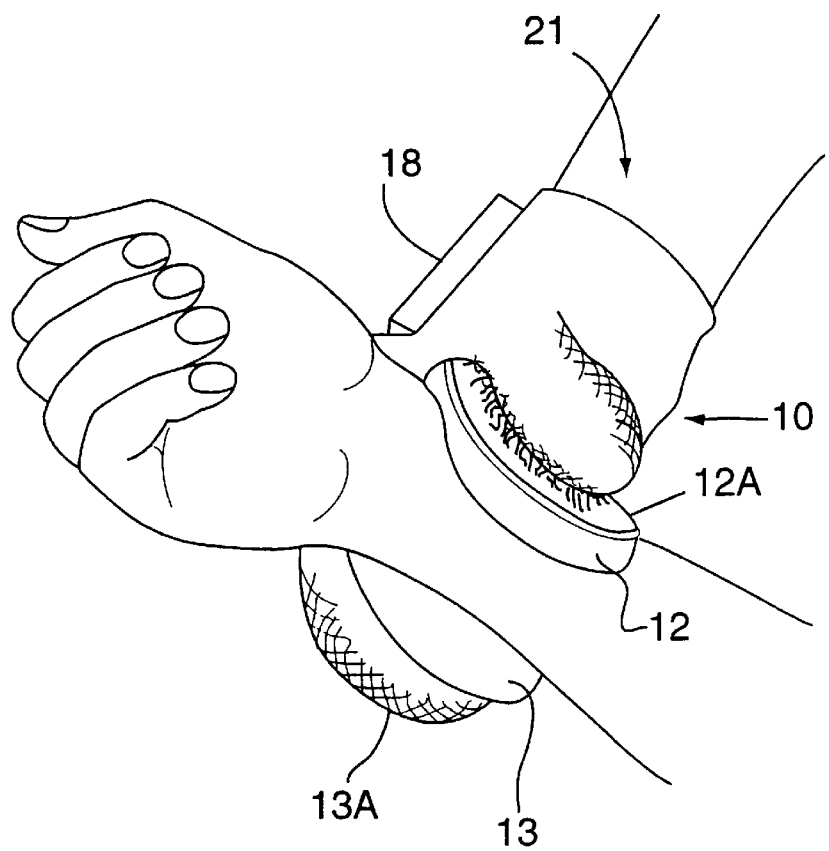
FIG. 2 is a schematic representation of a perspective view of one of the preferred embodiments of the device shown in FIG. 1, with the hand closed in a grip around the wrist of a test subject.

In FIG. 2, mitt 10 of FIG. 1 is shown in its preferred use i.e. that of evaluating the forces in a subject's forearm. The evaluator's hand, generally indicated by 21, grasps the subject's wrist through the mitt 10. The evaluator moves the subject's forearm back and forth to evoke reflexive forces or holds the forearm steady and instructs the subject to generate voluntary force. Either of such actions results in a pressure differential between the thumb and fingers of mitt 10, which is shown on display panel 19 of FIG. 1.

Figure 3:
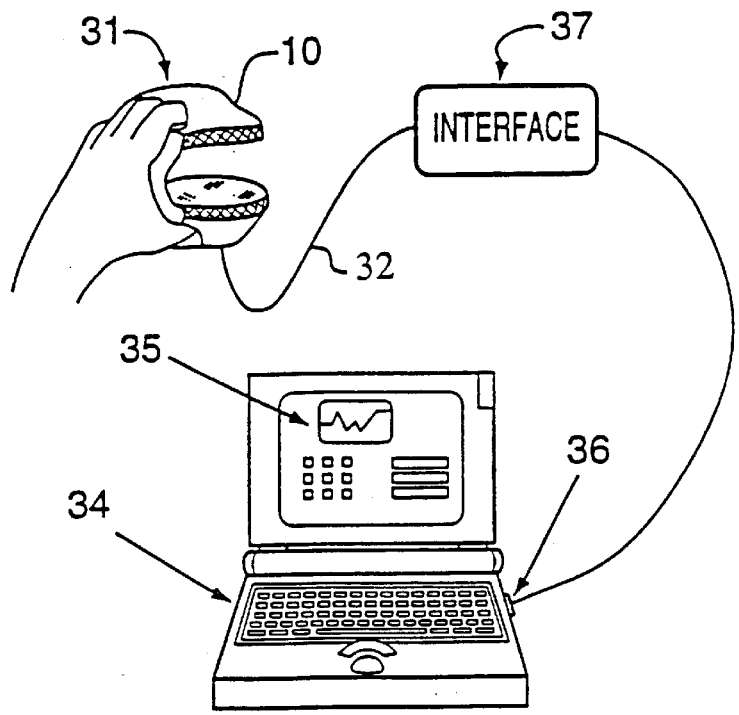
FIG. 3 is a schematic representation of two means of displaying and analyzing the monitored force signal from a preferred embodiment.

FIG. 3 shows two means of displaying and analyzing the resultant force signal in the preferred embodiment. Parameters of the signal may be displayed in numerical form on an electronic display panel 31 attached to mitt 10. Alternatively, the resultant force signal may be fed, by a cable schematically indicated by 32, through an interface box 37 containing a communications link to other data analysis devices, such as a laptop computer, 34, fitted with a data sampling card, 36. As shown, the analyzed data may be displayed on computer screen 35.

FIG. 4 shows an alternative embodiment of the device of FIG. 1, namely a spring-loaded cuff 41. The pressure pads are deployed on a springy U-piece designed to clip on to the wrist, as illustrated in FIG. 4, or ankle of the person being evaluated. An evaluator's hand 42 is shown as cupped around cuff 41. An additional sensor 43 permits displacement of the subject's limb to be sensed along with the force measurement described above. In a preferred embodiment, the displacement sensor is in the form of an extensible rubber band 44 attached at one end to a reference point on the patient's upper arm 45 and at the other end to a strain gauge element 46 in cuff 41. Electronic circuitry decodes the output of the strain gauge element 46 in cuff 41. In an alternative embodiment, the display sensor is in the form of a three-directional accelerometer inside cuff 41. Electronic circuitry decodes the output of the strain gauge or accelerometer into a displacement signal. This signal, when combined with the force signal, allows mechanical impedance of the test limb or object to be computed by external devices such as the computer system of FIG. 3. This computation might include parametric identification of viscous and elastic stiffness of the limb.

In operation, two fluid-filled pads 12 and 13 (see FIG. 1) are located on the inner or palmar surface of mitt 10 at the distal or end segments of the thumb and fingers, respectively. Tube 15 leads from each of these pads to a differential pressure transducer. The force applied by the thumb and the summed force applied by the fingers of the evaluator cause pressure changes in pads 12 and 13. If equal forces are applied to pads 12 and 13, as in a pinch grip with net zero force applied to the limb, the differential pressure transducer registers zero pressure difference. When there is a net force applied to the limb or object, the force is greater on one pad than on the other. This leads to a pressure difference between pads 12 and 13, and the resultant force is registered by the transducer in the form of a change in voltage. This may be displayed, as discussed above.

The force signal from the transducer may be displayed in a number of ways, including a digital display showing maximum force in each direction i.e. push and pull, a plot of the time course of the force signal or a plot of the force against some other measurable parameter e.g. displacement. The force signal may also be used in more complex analyses, for example of mechanical impedance and of frequency content.

Figure 5:
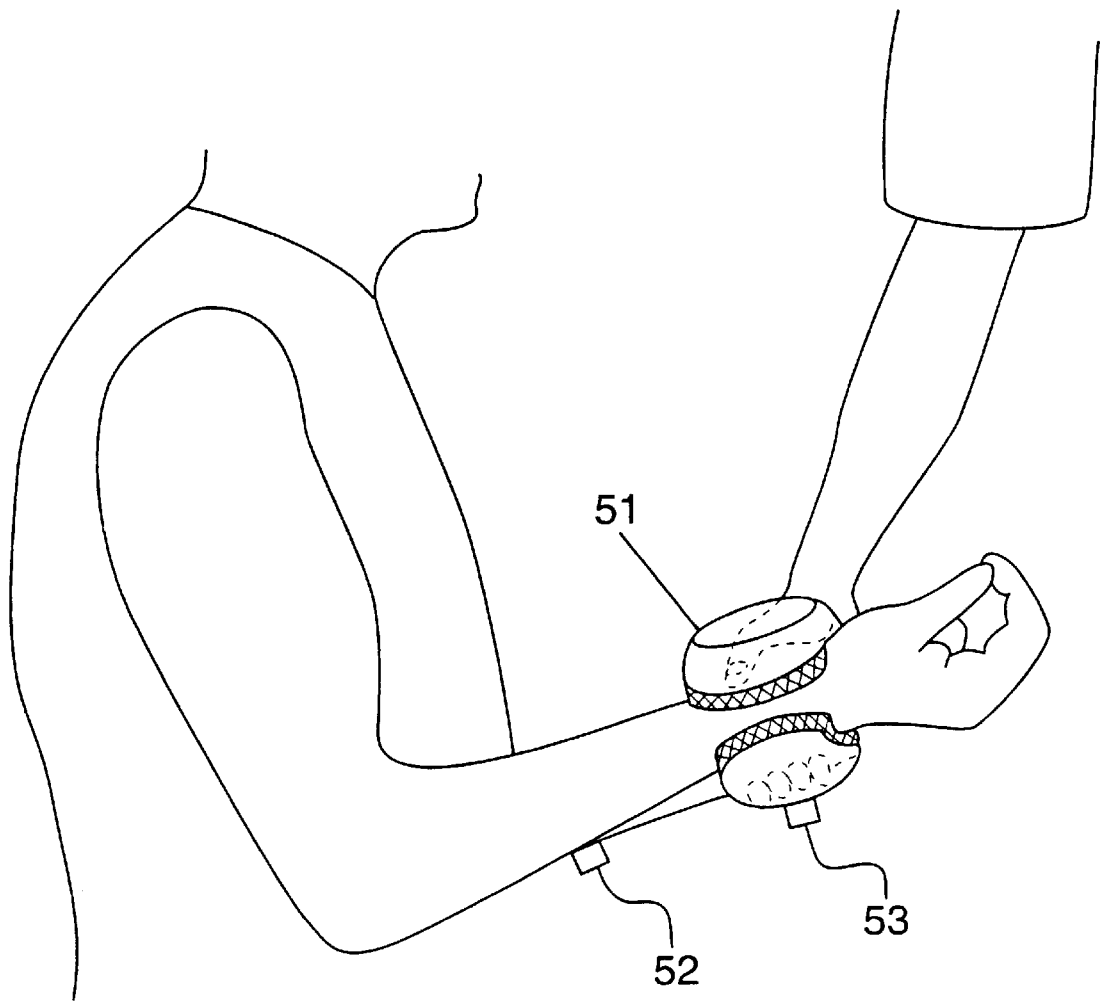
FIG. 5 is a schematic representation of an alternate embodiment of the mitt of FIG. 4.

FIG. 5 shows an alternate embodiment of the mitt of FIG. 4 in which the displacement sensor is in the form of a balanced pair of accelerometers, 52 and 53, deployed in such a way as to allow displacement to be derived mathematically or by signal conditioning from signals from the two accelerometers. Accelerometer 52 is mounted on a stiff rod or shaft protruding from force sensor housing 51. Movements of the arm of the user tilt both accelerometers 52 and 53 through the same angle with respect to the vertical. Thus, a subtraction of the signal from accelerometer 52 from that of accelerometer 53 cancels out that part of the response due to gravity. Furthermore, because the separation between accelerometers 52 and 53 is known and remains constant at all times, an algorithm e.g. that of Chizeck H. J., Stein R. B., Chang S., Scheiner A. and Ferencz D. C., may be used to derive the acceleration of accelerometer 53 alone, i.e. the acceleration of the point of application of the external force. Displacement may be determined mathematically, by double integration of the acceleration, which may be used to compute mechanical impedance, as discussed above.

In aspects of the mitt or cuff of the invention, at least one accelerometer is used in conjunction with pressure transducers, to allow parameters of mechanical impedance to be computed. The one accelerometer is preferably within or attached to the mitt or cuff. In embodiments, one or preferably two accelerometers are used.

To use the device, the evaluator dons mitt 10 and grasps the subject's limb or places the spring loaded cuff 41 on the limb and grasps the limb by cupping the hand around the cuff. Movements are then imposed on the limb, through the mitt or cuff. The force signal is displayed in the manner described above, providing the evaluator with diagnostically useful information.

The device is particularly useful in evaluation of limbs, especially mechanical properties of limbs, of persons with pathological rigidity due to neurological disorders such as Parkinson's disease, hemiplegia, multiple sclerosis, quadriplegia and paraplegia, and of persons with reduced range of motion due to sports injuries, arthritis or contractures.

We claim:

1. A force-sensing mitt or cuff which may be used to grasp a limb or other object, said mitt or cuff comprising pressure sensitive pads at at least two separate locations on said mitt or cuff to provide quantitative information on the difference in pressure applied to said limb or object between said locations, said mitt being in a form capable of fitting on a person's hand, with the pressure sensitive pads being located at positions corresponding to a thumb and to four fingers of the hand, said pressure sensitive pads having thin stiff sheets thereon to facilitate distribution of pressure over said pressure sensitive pads.

2. The mitt or cuff of claim 1 in which at least two pressure-sensitive pads are located within said mitt or cuff and deployed in such a way as to additionally separately sense the pressure applied to said limb or object at said two separate locations.

3. The mitt or cuff of claim 1 in which the pressure sensitive pads register zero pressure when equal pressure is applied at two opposed locations.

4. The mitt or cuff of claim 3 in which parameters measured are displayed on an electronic display built into said mitt or cuff.

5. The mitt or cuff of claim 4 in which the pressure sensitive pads comprise two pressure transducers.

6. The mitt or cuff or claim 1 in which a displacement transducer is used in conjunction with pressure transducers, to allow parameters of mechanical impedance to be computed.

7. The mitt or cuff of claim 1 in which at least one accelerometer is used in conjunction with pressure transducers, to allow parameters of mechanical impedance to be computed, said at least one accelerometer being within or attached to said mitt or cuff.

8. The mitt or cuff of claim 7 in which there is one accelerometer.

9. The mitt or cuff of claim 7 in which there are two accelerometers.

10. The mitt or cuff of claim 1 in which the pressure sensitive pads comprise at least two pressure transducers.

11. A medical device in the form of a garment having a first pressure transducer and a second pressure transducer, said first transducer and said second transducer being located on separate portions of the garment and being capable of contacting substantially opposed sides of an object or limb, each of said pressure transducers being connected to recording means capable of recording the difference in pressure measures by the pressure transducers, said first and second pressure transducers having thin stiff sheets thereon to facilitate distribution of pressure over the respective transducer.

12. The device of claim 11 in the form of a mitt.

13. The device of claim 11 in the form of a cuff.

* * * * *